United States Patent [19]
DeLeo

[11] Patent Number: 6,017,216
[45] Date of Patent: *Jan. 25, 2000

[54] ORTHODONTIC APPARATUS FOR ATTACHMENT TO TEETH

[76] Inventor: David B. DeLeo, 71 East Ave., Suite 2Q, Norwalk, Conn. 06851

[ * ] Notice: This patent is subject to a terminal disclaimer.

[21] Appl. No.: 09/188,488

[22] Filed: Nov. 9, 1998

Related U.S. Application Data

[63] Continuation of application No. 08/958,790, Oct. 29, 1997, Pat. No. 5,879,156.

[51] Int. Cl.[7] ...................................................... A61C 3/00
[52] U.S. Cl. ................................................................... 433/9
[58] Field of Search ................................. 433/2, 8, 9, 10, 433/23

[56] References Cited

U.S. PATENT DOCUMENTS

| | | | |
|---|---|---|---|
| 4,165,561 | 8/1979 | Miller et al. | 433/9 |
| 4,659,309 | 4/1987 | Merkel | 433/9 |
| 4,749,352 | 6/1988 | Nicholson | 433/9 |
| 4,842,513 | 6/1989 | Haarmann | 433/9 |
| 4,878,840 | 11/1989 | Reynolds | 433/9 |
| 5,439,379 | 8/1995 | Hansen | 433/9 |
| 5,607,299 | 3/1997 | Nicholson | 433/8 |
| 5,879,156 | 3/1999 | DeLeo | 433/9 |

*Primary Examiner*—Ralph A. Lewis
*Attorney, Agent, or Firm*—H. Gibner Lehmann; K. Gibner Lehmann

[57] ABSTRACT

An orthodontic bracket apparatus for attachment to a tooth, consisting of a flexible attachment pad having dimensions that are commensurate with a designated area of the tooth to which the apparatus is to be secured. The apparatus has a pair of brackets permanently mounted on adjoining areas at one side of the pad in spaced relation to each other, such brackets being maintained in their attached positions and separated by an elongate, narrow hinge portion of the pad, which portion is free from direct attachment to the brackets. The narrow hinge portion of the ductile pad enables an initial easy, relative arcuate adjusting movement of the brackets to be effected with respect to each other, thereby to obtain a closer fit of the entire pad to the surface contours of the tooth which is to have the apparatus affixed to its surface.

14 Claims, 1 Drawing Sheet

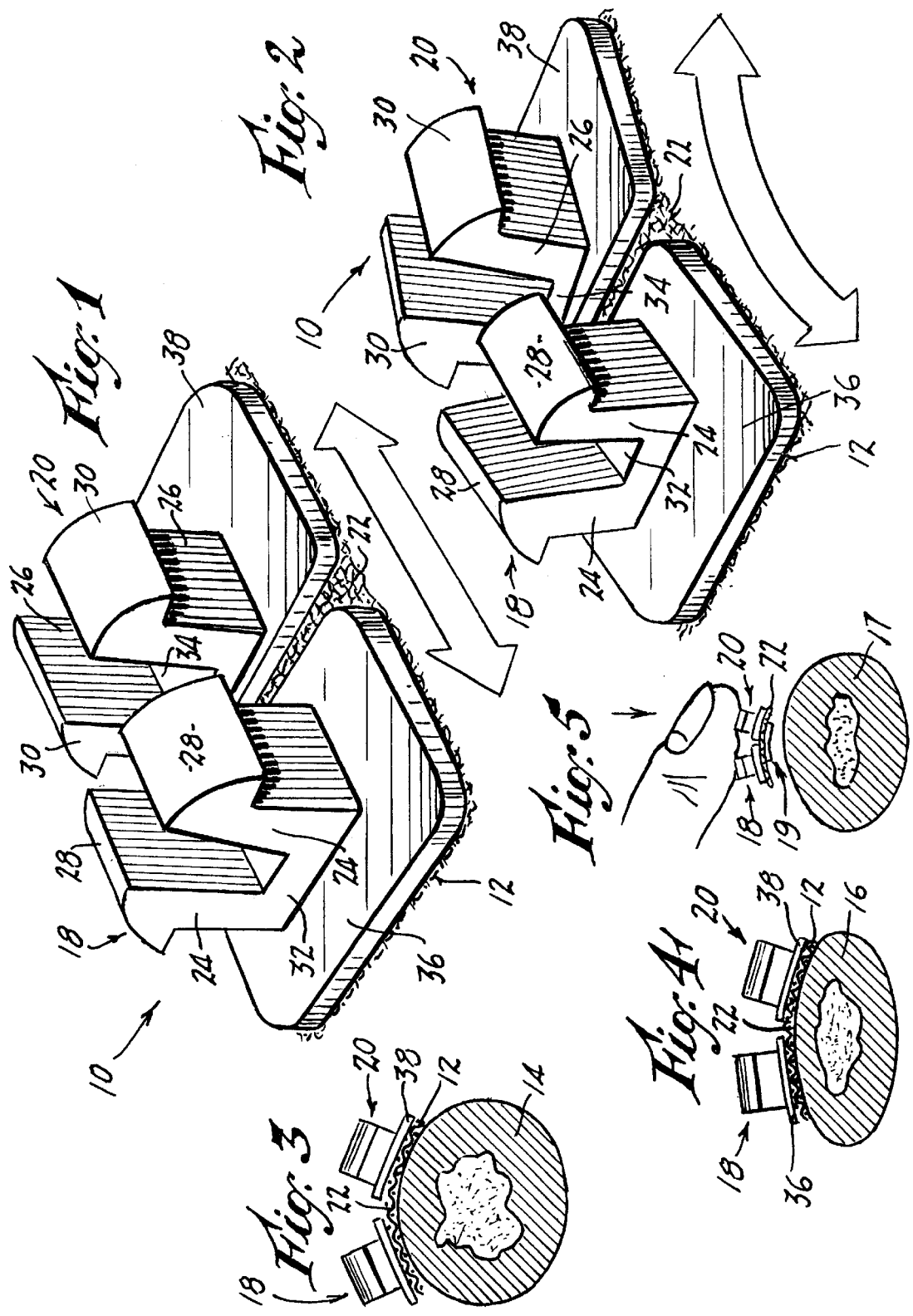

6,017,216

ORTHODONTIC APPARATUS FOR ATTACHMENT TO TEETH

CROSS REFERENCES TO RELATED APPLICATIONS/PATENTS

The present application is a continuation of my U.S. application Ser. No. 08/958,790 filed Oct. 29, 1997, now U.S. Pat. No. 5,879,156, and issued Mar. 9, 1999, having common ownership with the present application.

STATEMENT AS TO RIGHTS TO INVENTIONS MADE UNDER FEDERALLY-SPONSORED RESEARCH AND DEVELOPMENT

Research and development of the present invention and application have not been Federally-sponsored, and no rights are given under any Federal programs.

BACKGROUND OF THE INVENTION

Field of the Invention

This invention relates to orthodontic apparatuses for attachment to teeth, for the purpose of positioning or straightening the teeth, the latter with the use of applied forces.

In the past numerous devices have been proposed and produced, intended to be cemented or glued to teeth in the mouth to enable wires or springs and the like to be used for applying forces to certain teeth to correct alignment thereof.

U.S. Pat. Nos. 3,250,003 and 4,068,379 disclose examples of some of these prior bracket devices. The disclosed devices, while explaining certain improvements, had several drawbacks. For one thing, because of a faulty fit of the device to the variable tooth contour, voids or cavities often existed under the device after the attachment was effected. These voids required filling to avoid collection of food, and the practice was to apply a temporary filler thereto so as to present a smooth dentally acceptable surface.

In order to insure a strong bond of the bracket to the tooth, a base member was used which had appreciable surface area. The larger the surface area, the better the chances were for the bond to be effective. However, larger surface areas meant that the voids under the device also became larger, since the base portions of the brackets were rigid and not in conformance with the tooth contours.

In some instances this was overcome by the use of flexible bands which were wrapped around the tooth. However, this was not always feasible or practical, or comfortable to the patient.

The above disadvantages and drawbacks of prior orthodontic attachments for securement to teeth in the mouth are overcome by the present invention, and one object of the invention is to provide an improved orthodontic apparatus for attachment to teeth, which is readily adjustable prior to or during its securement thereof so as to enable a better fit to be had of the apparatus to the surface contours of the various kinds of teeth found in the mouth.

Another object of the invention is to provide an improved orthodontic apparatus as above set forth, which is especially simple and economical to produce.

A further object of the invention is to provide an improved apparatus in accordance with the foregoing, which is easy to adjust and which provides a greatly improved fit to tooth contours.

A feature of the invention resides in the improved apparatus as characterized, which effects an improved bond and adhesion of the apparatus to the tooth.

Another object of the invention is to provide an improved and simplified process by which an orthodontic apparatus is fitted and applied to a tooth so as to more closely conform to the tooth contour.

The above objectives are accomplished by an orthodontic bracket apparatus for attachment to a tooth, consisting of a flexible attachment pad having dimensions that are commensurate with a designated area of the tooth to which the apparatus is to be secured. The apparatus has a pair of brackets permanently mounted on adjoining areas at one side of the pad in spaced relation to each other, such brackets being maintained in their attached positions and separated by an elongate, narrow hinge portion of the pad, which portion is free from direct attachment to the brackets. The narrow hinge portion of the ductile pad enables an initial easy, relative arcuate adjusting movement of the brackets to be effected with respect to each other, thereby to obtain a closer fit of the entire pad to the surface contours of the tooth which is to have the apparatus affixed to its surface.

Other features and advantages will hereinafter appear.

In the accompanying drawings:

FIG. 1 is a perspective view of the improved orthodontic apparatus of the invention, showing one adjusted position of the brackets thereof with an arrow to indicate the adjusted position.

FIG. 2 is a perspective view like FIG. 1, but showing another adjusted position of the brackets and attachment pad.

FIG. 3 is a cross section of a tooth such as a cuspid, having attached to it the improved apparatus of the invention.

FIG. 4 is a cross section of a tooth such as an incisor, having attached to it the apparatus of the invention in another adjusted position of the brackets and pad thereof and FIG. 5 is a view like that of FIG. 4, illustrating the process of applying the apparatus to a tooth.

Referring first to FIGS. 1 and 2, the improved orthodontic apparatus 10 of the invention comprises a new combination of flexible and preferably foraminous attachment pad 12 that mounts uniquely placed orthodontic brackets by which an adjustable configuration of the pad is possible, thereby to enable the apparatus to have a better fit with various tooth curvatures.

The pad 12 can be of ductile wire mesh, and can have dimensions which are commensurate with a designated or predetermined area of the tooth to which the pad is to be affixed.

Two such teeth, designated as 14 and 16, are shown in FIGS. 3 and 4. The cross section of the tooth 14 as seen in FIG. 3 is essentially circular, whereas the cross section of the tooth 16 in FIG. 4 is oval shaped. It follows that the surface contours of the tooth 14 are quite different from the surface contours of the tooth 16, and that any attempted close fit of an unyielding base plate portion of a conventional tooth bracket of the type having four posts or wings could not at one and the same time be very successful when considering both of the above pointed out different surface contours of the teeth 14, 16.

In accordance with the present invention the flexible pad 12 has permanently mounted on it, on adjoining areas thereof, a pair of orthodontic brackets 18 and 20 which brackets are in spaced relation to each other, both brackets being on one side of the pad as shown in FIG. 1. The brackets 18 and 20 are positioned in the said attached relation on the pad 12 by an elongate, narrow portion 22 of the pad, which portion is notably free of direct attachment to the pad.

This narrow portion 22 of the pad functions very much like a living hinge, except that it is ductile as distinguished from being resilient, thereby enabling an advantageous, easily carried out relative arcuate adjusting movement of the brackets 18 and 20 to be effected with respect to each other. The narrow portion thus constitute a means permanently attaching the brackets to adjoining areas of the pad and in spaced relation to each other. By such organization, the pad 12 can be quickly, quite closely fitted to various different surface contours of different teeth, as for example, the teeth 14 and 16 shown in FIGS. 3 and 4.

By having a better fit of the pad 12 there is accomplished better adhesion of the pad 12 to the tooth surface, and also undesirable voids are eliminated at the pad edges, which would otherwise require filling to present a smooth dental surface on the tooth, free from cavities.

The portion of the pad 12 which lies under the base member 36, through the medium of the narrow hinge pad portion 22, adds support to that portion of the pad 12 which lies under the base member 38, and the latter adds support to that portion of the pad 12 which lies under the base member 36. In other words, these pad portions are mutually helpful to each other in enabling the brackets 18 and 20 to remain attached to the tooth.

The brackets 18 and 20 each comprise pairs of posts 24 and 26, with hooked extremities 28 and 30 and yoke portions 32 and 34. The yoke portions 32 and 34 mount the brackets 18 and 20 on base plates 36 and 38. The brackets 18 and 20 can be integral with their base plates 36 and 38, or else attached thereto by adhesive, or welding, brazing, soldering and the like.

The pad 12 can be constituted of ductile or soft metal mesh, and the mounting of the base plates 36 and 38 on the pad 12 can be effected by an adhesive, or by welding, brazing, soldering and the like. Any mounting procedure should not adversely affect the ability of the hinge portion 22 of the pad to permit limited arcuate adjusting movement of the brackets 18 and 20 with respect to each other.

FIG. 2 illustrates such adjusting movement where the brackets 18 and 20 are arcuately separated to an extent. This results in angular deformation of the pad 12 to enable it to be more closely fitted to a well rounded tooth contour as shown in FIG. 3. Where the tooth contour is flatter, as in FIG. 4, the pad 12 can be flattened somewhat as seen in FIGS. 1 and 4, compared to the showing of FIG. 3. In each instance, a better fit can be established between the pad 12 and the tooth surface, resulting in better adhesion and an absence of large voids that would require extensive filling, which is time consuming and non-productive.

The improved method of fitting and attaching a bracket device, such as the bracket apparatus 10, to a tooth is illustrated in FIG. 5. In this figure the tooth 17 has a surface which is relatively flat, and the bracket apparatus having brackets 18 and 20 connected to each other by the flexible mesh 22, has a preset curvature which is greater than the curvature of the tooth 10. A small quantity of adhesive 19 is applied to the underside of the mesh 22, and the apparatus is then pressed into forcible contact with the tooth. This will flatten somewhat the mesh 22, causing it to conform more closely to the tooth contour. The apparatus is held by the operator's hand in the proper position against the tooth until the adhesive has had time to set somewhat. By this procedure a closer and more effective bond is established between the apparatus and the tooth.

It will now be understood that no difficult manufacturing processes are required to carry out the present invention, and that a surprising improvement is realized in the better quality of work, and in the saving of time.

Each and every one of the appended claims defines an aspect of the invention which is complete in and of itself, separate and distinct from all others, and accordingly it is intended that each claim be treated in this manner when examined in the light of the prior art devices in any determination of novelty or validity.

Variations and modifications are possible without departing from the spirit of the invention, and parts of the invention can be used without others.

What is claimed is:

1. An orthodontic apparatus for attachment to a tooth, comprising, in combination:
   a) a flexible, essentially non-resilient attachment pad having dimensions which are commensurate with a designated area of the tooth to which the pad is to be affixed, and
   b) a pair of orthodontic brackets attached to adjoining areas of the flexible pad in spaced relation to each other and on one side of the pad,
   c) said brackets being held in said attached positions and separated by an elongate narrow portion of said pad, which portion is free of direct attachment to the brackets,
   d) said narrow portion enabling a relative arcuate adjusting movement of the brackets to be effected with respect to each other, thereby to obtain a closer fit of the pad to the surface contour of the tooth which is to have the apparatus affixed to its surface.

2. An orthodontic apparatus for attachment to a tooth, as set forth in claim 1, wherein the pad is foraminous.

3. An orthodontic apparatus for attachment to a tooth, as set forth in claim 1, wherein the pad comprises metal mesh.

4. An orthodontic apparatus for attachment to a tooth, as set forth in claim 3, wherein the metal of the mesh is soft and ductile.

5. An orthodontic apparatus for attachment to a tooth, as set forth in claim 1, wherein the brackets have expansive base plates.

6. An orthodontic apparatus for attachment to a tooth, as set forth in claim 5, wherein the brackets are cemented to the base plates.

7. An orthodontic apparatus for attachment to a tooth, as set forth in claim 5, wherein the brackets are spot welded to the base plates.

8. An orthodontic apparatus for attachment to a tooth, as set forth in claim 1, wherein the brackets are constituted of cast metal.

9. An orthodontic apparatus for attachment to a tooth, as set forth in claim 5, wherein the brackets are brazed to the base plates.

10. An orthodontic apparatus for attachment to a tooth, a; set forth in claim 5, wherein the brackets are soldered to the base plates.

11. An orthodontic apparatus for attachment to a tooth, as set forth in claim 1, wherein the pad straddles and bridges the gap between the base plates.

12. An orthodontic apparatus for attachment to a tooth, as set forth in claim 1, wherein said narrow portion of the pad constitutes a hinge about which the brackets can swivel with respect to one another.

13. An orthodontic apparatus for attachment to a tooth, as set forth in claim 1, wherein all portions of the pad are integral with one another.

14. An orthodontic apparatus for attachment to a tooth, comprising, in combination:

a) a flexible, essentially non-resilient attachment pad having dimensions which are commensurate with a designated area of the tooth to which the pad is to be affixed, and
b) a pair of orthodontic brackets attached to adjoining areas of the flexible pad in spaced relation to each other and on one side of the pad,
c) said brackets being held in said attached positions and separated by an elongate narrow portion of said pad, which elongate narrow portion is free of direct attachment to the brackets,
d) said narrow portion enabling a relative arcuate adjusting movement of the brackets to be effected with respect to each other, thereby to obtain a closer fit of the pad to the surface contour of the tooth which is to have the apparatus affixed to its surface.

* * * * *